(12) United States Patent
Mukhopadhyay et al.

(10) Patent No.: US 9,035,111 B2
(45) Date of Patent: *May 19, 2015

(54) METHOD FOR PRODUCING FLUORINATED ORGANIC COMPOUNDS

(75) Inventors: Sudip Mukhopadhyay, Berkeley, CA (US); Cheryl L. Bortz, North Tonawanda, NY (US); Kim M. Fleming, Hamburg, NY (US); Steven D. Phillips, Buffalo, NY (US); Rajesh K. Dubey, Williamsville, NY (US)

(73) Assignee: HONEYWELL INTERNATIONAL INC., Morristown, NJ (US)

( * ) Notice: Subject to any disclaimer, the term of this patent is extended or adjusted under 35 U.S.C. 154(b) by 1713 days.

This patent is subject to a terminal disclaimer.

(21) Appl. No.: 12/196,207

(22) Filed: Aug. 21, 2008

(65) Prior Publication Data

US 2009/0203945 A1 Aug. 13, 2009

Related U.S. Application Data

(63) Continuation-in-part of application No. 11/619,592, filed on Jan. 3, 2007, now Pat. No. 8,084,653, which is a continuation-in-part of application No. 11/118,503, filed on Apr. 29, 2005, now Pat. No. 7,345,209, and a continuation-in-part of application No. 11/118,504, filed on Apr. 29, 2005, now Pat. No. 7,371,904, and a continuation-in-part of application No. 11/118,530, filed on Apr. 29, 2005, now Pat. No. 7,189,884.

(60) Provisional application No. 60/957,193, filed on Aug. 22, 2007, provisional application No. 60/755,485, filed on Jan. 3, 2006, provisional application No. 60/567,427, filed on Apr. 16, 2004, provisional application No. 60/567,425, filed on Apr. 16, 2004, provisional application No. 60/567,426, filed on Apr. 16, 2004, provisional application No. 60/567,429, filed on Apr. 16, 2004, provisional application No. 60/567,428, filed on Apr. 29, 2004.

(51) Int. Cl.
| | | |
|---|---|---|
| *C07C 21/18* | (2006.01) | |
| *C07C 17/38* | (2006.01) | |
| *C07C 17/04* | (2006.01) | |
| *C07C 17/20* | (2006.01) | |
| *C07C 17/21* | (2006.01) | |
| *C07C 17/25* | (2006.01) | |

(52) U.S. Cl.
CPC ............... *C07C 17/38* (2013.01); *C07C 17/04* (2013.01); *C07C 17/206* (2013.01); *C07C 17/21* (2013.01); *C07C 17/25* (2013.01); *C07C 21/18* (2013.01)

(58) Field of Classification Search
None
See application file for complete search history.

(56) References Cited

U.S. PATENT DOCUMENTS

| | | | |
|---|---|---|---|
| 2,931,840 A | | 4/1960 | Marquis |
| 4,900,874 A | | 2/1990 | Ihara et al. |
| 7,189,884 B2 * | | 3/2007 | Mukhopadhyay et al. ... 570/160 |
| 8,058,486 B2 * | | 11/2011 | Merkel et al. ................. 570/155 |
| 8,067,649 B2 * | | 11/2011 | Kopkalli et al. ............... 570/155 |
| 8,071,825 B2 * | | 12/2011 | Johnson et al. ................ 570/155 |
| 8,084,653 B2 * | | 12/2011 | Tung et al. .................... 570/123 |
| 2007/0129579 A1 * | | 6/2007 | Wang et al. ................... 570/155 |
| 2009/0124837 A1 * | | 5/2009 | Mukhopadhyay et al. ... 570/167 |

FOREIGN PATENT DOCUMENTS

| | | |
|---|---|---|
| WO | WO2007/079431 | 7/2007 |
| WO | WO-2007079435 * | 7/2007 |

OTHER PUBLICATIONS

RN Haszeldine, Journal of the Chemical Society., 1951, pp. 2495-2504, XP002503499.

Banks et al., Preparation of 2,3,3,3-Tetrafluoropropene From Trifluoroacetylacetone and Sulphur Tetrafluoride, Journal of Fluorine Chemistry, 1997, 171-174, vol. 82, Manchester, UK.

* cited by examiner

*Primary Examiner* — Clinton Brooks
(74) *Attorney, Agent, or Firm* — Bruce Bradford

(57) ABSTRACT

A method for producing fluorinated organic compounds, including hydrofluoropropenes, which preferably comprises converting at least one compound of formula (I):

$$CF_3(-CX^2X^2)_nCX^1=H_2 \qquad (I)$$

to at least one compound of formula (II):

$$CF_3(CX^2X^2)_nCX^1=H_2 \qquad (II),$$

where $X^1$ is Cl, Br or I, each $X^2$ is independently selected from the group consisting of H, Cl, F, Br or J, and n is 0, 1, or 2.

11 Claims, No Drawings ered to be tetrafluoropropenes (including particularly 2,3,

METHOD FOR PRODUCING FLUORINATED ORGANIC COMPOUNDS

CROSS-REFERENCE TO RELATED APPLICATIONS

This application claims the priority benefit of pending U.S. Provisional Application No. 60/957,193, filed Aug. 22, 2007, which is incorporated herein by reference. The present application is also a continuation-in-part of U.S. patent application Ser. No. 11/619,592, filed Jan. 3, 2007 (now U.S. Pat. No. 8,084,653), which claims the priority benefit of U.S. Provisional Application No. 60/755,485, filed Jan. 3, 2006. U.S. patent application Ser. No. 11/619,592 also claims priority as follows: (1) as a continuation-in-part of U.S. patent application Ser. No. 11/118,503, (now U.S. Pat. No. 7,345,209) filed on Apr. 29, 2005, which in turn claims the priority benefit of U.S. Provisional Patent Application Nos. 60/567,427 and 60/567,425 filed Apr. 16, 2004; (2) as a continuation-in-part of U.S. patent application Ser. No. 11/118,504, (now U.S. Pat. No. 7,371,904) filed on Apr. 29, 2005, which in turn claims the priority benefit of U.S. Provisional Patent Application Nos. 60/567,426 and 60/567,429 filed Apr. 16, 2004; and (3) as a continuation-in-part of U.S. patent application Ser. No. 11/118,530, (now U.S. Pat. No. 7,189,884) filed on Apr. 29, 2005, which in turn claims the priority benefit of U.S. Provisional Patent Application No. 60/567,428 filed Apr. 29, 2004.

BACKGROUND OF INVENTION (1) Field of Invention

This invention relates to novel methods for preparing fluorinated organic compounds, and more particularly to methods of producing fluorinated olefins, and even more particularly to methods of preparing 2,3,3,3-tetrafluoro-1-propene (HFO-1234yf).

(2) Description of Related Art

Hydrofluorocarbons (HFCs), in particular hydrofluoroalkenes such astetrafluoropropenes (including particularly 2,3, 3,3-tetrafluoro-1-propene (HFO-1234yf) have been disclosed to be effective refrigerants, fire extinguishants, heat transfer media, propellants, foaming agents, blowing agents, gaseous dielectrics, sterilant carriers, polymerization media, particulate removal fluids, carrier fluids, buffing abrasive agents, displacement drying agents and power cycle working fluids. Unlike chlorofluorocarbons (CFCs) and hydrochlorofluorocarbons (HCFCs), both of which potentially damage the Earth's ozone layer, HFCs do not contain chlorine and thus pose no threat to the ozone layer.

Several methods of preparing hydrofluoroalkenes are known. For example, U.S. Pat. No. 4,900,874 (Ihara et al) describes a method of making fluorine containing olefins by contacting hydrogen gas with fluorinated alcohols. Although this appears to be a relatively high-yield process, for commercial scale production the handling of hydrogen gas at high temperature raises difficult safety related questions. Also, the cost of producing hydrogen gas, such as building an on-site hydrogen plant, can be in many situations prohibitive.

The '874 patent also describes in the background a process for producing fluorinated olefins by a process which includes reacting a fluorinated alkane with zinc as follows:

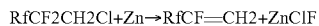

However, this reaction is identified as having various disadvantages, including (1) having a slow reaction rate based on the use of a chloride, (2) the need to dispose of the organic solvent typically used in such reactions, and (3) the problem of having to dispose of the by-product of zinc halide.

U.S. Pat. No. 2,931,840 (Marquis) describes a method of making fluorine containing olefins by pyrolysis of methyl chloride and tetrafluoroethylene or chlorodifluoromethane. This process is a relatively low yield process and a very large percentage of the organic starting material is converted in this process to unwanted and/or unimportant byproducts, including a sizeable amount of carbon black. The carbon black is not only unwanted, it tends to deactivate the catalyst used in the process.

The preparation of R-1234yf from trifluoroacetylacetone and sulfur tetrafluoride has been described. See Banks, et al., *Journal of Fluorine Chemistry*, Vol. 82, Iss. 2, p. 171-174 (1997). Also, U.S. Pat. No. 5,162,594 (Krespan) discloses a process wherein tetrafluoroethylene is reacted with another fluorinated ethylene in the liquid phase to produce a polyfluoroolefin product.

Notwithstanding prior teachings applicants appreciate a continuing need for methods of efficiently preparing certain hydrofluorocarbons, particularly tetrafluoropropenes such as HFO-1234yf.

SUMMARY OF THE INVENTION

Applicants have discovered a method for producing fluorinated organic compounds, including hydrofluoropropenes, which preferably comprises converting at least one compound of formula (I):

to at least one compound of formula (II)

where $X^1$ is Cl, Br or I, each $X^2$ is independently selected from the group consisting of H, Cl, F, Br or I, and n is 0, 1 or 2. In certain preferred embodiments, $X^1$ is Cl and n is 0.

In one broad aspect, it is contemplated that a wide variety of reaction conditions may be used for the converting step. For example, it is contemplated that the converting step may comprise in certain embodiments a gas phase reaction, with or without catalyst, a liquid phase reaction, with or without catalyst, and combinations of these two. However, applicants have found that exceptional results can be obtained according to certain embodiments in which the converting step comprises at least a first reaction step followed by a second reaction step to achieve relatively high overall levels of conversion of the compound of formula (J) and relatively high overall selectivity to the compound of formula (II).

DETAILED DESCRIPTION OF PREFERRED EMBODIMENTS

One beneficial aspect of the present invention is that it enables the production of desirable fluoroolefins, preferably C3 fluoroolefins, from relatively attractive starting materials, and in preferred embodiments the present methods are capable of achieving very desirable levels of conversion of the starting materials while also providing high levels of selectivity to the desired products. Chlorofluoroolefins, and preferably 2-chloro-3,3,3-trifluoropropene (HFCO-1233xf), are in many embodiments an advantageous starting material because such products are relatively inexpensive, are relatively easy to handle, and are generally readily available in commercial quantities or can be easily produced from other readily available materials. For example, such products, particularly 2-chloro-3,3,3-trifluoropropene, may be formed by addition of chlorine to the unsaturated non-terminal carbon of 3,3,3-trifluoropropene to produce CF$_3$CHClCH$_2$Cl, which is in turn is converted to a desired reactant 2-chloro-3,3,3-trifluoropropene.

Thus, in certain embodiments the present methods include the step of forming the compound of formula (J) by reacting fluorinated C3 olefin, such as trifluoropropene, with a halogen addition agent, preferably a chlorine addition agent, under conditions effective to produce a compound of formula (A)

CF$_3$(CX$^2$X$^2$)$_n$CHXCH$_2$X$^1$ (A)

where X$^1$, X$^2$, and n are each as described above. In preferred embodiments, X is Cl and n is 0. The compound of formula (A) is then converted, preferably by hydrohalogenation, to a compound of formula (I).

Once the compound of formula (I) is provided, either by steps of the type referred to above, by other process steps, or by simple purchase of the compound, it is converted to a compound of formula (II). It is contemplated, although not necessarily preferred, that the conversion step can take place under reaction conditions that utilize a single set or range of reaction conditions, and such a step is sometimes referred to herein for convenience, but not necessarily by way of limitation, as a one step reaction. Such one step reactions preferably include two or more reaction mechanisms, such as an addition and an exchange. Preferably, the one step process involves an additional reaction, such as fluorination and the like, followed by an exchange reaction, such as dehydrohalogenation and the like.

However, applicants have found that in certain of such one step reaction embodiments the conversion of the compound of formula (I) and/or the selectivity to a compound for formula (II) are relatively low. Applicants have found that it is generally preferred for the present methods to comprise exposing the compound of formula (I) to a first set or range of reaction conditions and to then expose the reaction product, or at least a portion thereof, to at least a second set of reaction conditions which produce a compound of formula (II). Such embodiments are sometimes referred to herein for convenience, but not necessarily by way of limitation, as multi-step reaction processes. Such multi-step reactions preferably include two or more reaction mechanisms, such as an addition and an exchange. Preferably, the multi-step process involves an additional reaction, such as fluorination and the like, followed by an exchange reaction, such as dehydrohalogenation and the like. The individual steps of a multi-step process may all be conducted in a single reactor—such as a multi-stage reactor, or in multiple reactors that operate in series, parallel, or some combination of the two.

In preferred aspects of the multi-stage reaction processes of present invention, the compound of formula (J) is exposed to conditions effective to produce, and preferable at relatively high rates of conversion and/or at high rates of selectivity, a saturated compound having a degree of fluorine substitution greater than the compound of formula (I), and preferably to produce at least one compound in accordance with Formula (B):

CF$_3$(CX$^2$X$^2$)$_n$CYYCH$_3$ (B)

where X$^2$ and n are each as described above and each Y is independently F, Cl, Br or I, provided that at least one Y is F. A preferred reaction by which the compound of formula (I) is converted to a compound of formula (B) is sometimes referred to herein for convenience, but not necessarily by way of limitation, as a fluorine addition reaction.

Preferably, at least a portion of the reaction product from the first set of reaction conditions, and preferably a reaction product comprising at least one compound of formula (B), is then exposed to conditions effective to produce, and preferable at relatively high rates of conversion and/or selectivity, a reaction product containing one or more of the desired fluoroolefins, preferably one or more compounds of formula (II). A preferred reaction by which the compound of formula (B) is converted to a compound of formula (II) is sometimes referred to herein for convenience, but not necessarily by way of limitation, as a dehydrofluorination reaction. Preferred aspects of each of the preferred steps are described below, with the titles used as headings for these steps being used for convenience but not necessarily by way of limitation.

I. Single Step Conversion Reaction

It is contemplated that the single step conversion may be performed using a wide variety of process parameters and process conditions in view of the overall the teachings contained herein. However, it is preferred in certain embodiments that this single step reaction comprise a gas phase reaction, preferably in the presence of catalyst, preferably a metal catalyst, and even more preferably one or more transition metal-based catalysts (including in certain preferred embodiments transition metal halide catalysts), such as FeCl$_3$, chromiumoxide, chromiumfluoride, chromiumoxyfluoride, Ni (including Ni mesh), NiCl$_2$, CrF$_3$, V$_2$O$_5$, MgO, and mixtures thereof, supported or in bulk. Other catalysts include carbon-based (such as activated carbon) and carbon-supported catalysts, antimony-based catalysts (such as SbF$_5$, Sb/Cl$_4$ and Sb/Cl$_5$), titanium-based catalysts (such as TiCl$_4$), aluminum-based catalyst (such as AlF$_3$ and Al$_2$O$_3$). It is expected that many other catalysts may be used depending on the requirements of particular embodiments including, for example, palladium-based catalysts (such as Pd/Al$_2$O$_3$), platinum-based catalysts, rhodium-based catalysts and ruthenium-based catalysts (such as Ru/Al$_2$O$_3$). Of course, two or more of any of these catalysts, or other catalysts not named here, may be used in combination.

In general it is preferred that the catalysts are fluorinated and/or chlorinated. In preferred embodiments, fluorination of the catalysts comprises exposing the catalyst to a stream of HF at about reaction temperature and pressure.

The single step conversion reaction may be conducted, for example, by introducing a gaseous form of a compound of formula (I) into a suitable reaction vessel or reactor. Preferably the vessel is comprised of materials which are resistant to corrosion as Hastelloy, Inconel, Monel and/or fluoropolymers linings. Preferably the vessel contains catalyst, for example a fixed or fluid catalyst bed, packed with a suitable catalyst, with suitable means to heat the reaction mixture to the desired reaction temperature.

While it is contemplated that a wide variety of reaction temperatures may be used, depending on relevant factors, such as, the catalyst being used and the most desired reaction product, it is generally preferred that the reaction temperature for the single step conversion reaction is from about 20° C. to about 600° C., preferably about 50° C. to about 550° C., and even more preferably from about 300° C. to about 550° C.

In general, it is also contemplated that a wide variety of reaction pressures may be used, depending again on relevant factors such as the specific catalyst being used and the most desired reaction product. The reaction pressure can be, for example, superatmospheric, atmospheric or under vacuum, with a reactor pressure of from about 0 to about 10 psig being preferred in certain embodiments.

In certain embodiments, an inert diluent gas, such as nitrogen, may be used in combination with the compound of formula (I) and the fluorinating agent, such as HF. When such a diluent is used, it is generally preferred that the mole ratio of formula (I) compounds to diluent is from about 1:2 to about 50:1.

It is contemplated that the amount of catalyst use will vary depending on the particular parameters present in each embodiment, and it is contemplated that those skilled in the art will be able to determine operable ranges without undue experimentation in view of the teachings contained herein.

Preferably in such one step reaction conditions the conversion is at least about 5%, more preferably at least about 10%, and even more preferably at least about 20%. Preferably, the selectivity to HFO-1234yf is at least about 70%, more preferably at least about 80% and more preferably at least about 90%.

II. Multi-Step Conversion Reaction

As mentioned above, preferred aspects of the present invention involve a conversion process that comprises a first reaction step and at least a second reaction step. Preferred embodiments of the first reaction step comprise a fluorine addition reaction and preferred forms of the second reaction step comprise a dehydrohalogenation reaction. Each of these preferred steps is described in detail below.

A. Fluorine Addition

In preferred embodiments, the reactant compound of formula (I) is a hydrofluorochloroolefin, more preferably hydrofluorochloropropene and even more preferably $CF_3CCl=CH_2$. It is further preferred that the fluorine addition agent is a compound of formula $X^1X^1$ where each $X^1$ is independently H, Cl, F, I or Br, provided at least one $X^1$ is F. Preferably, the fluorine addition agent comprises one or more of ClF, $F_2$ and HF.

For embodiments directed primarily to the production of $CF_3CF=CH_2$ (HFO-1234yf), it is generally preferred that the compound of formula (I) is reacted under conditions effective to produce at least one compound of formula (B1)

$$CF_3CF_nY_mCH_3 \quad (B1),$$

where Y is F, Cl, Br or I, n is 1 or 2, m is 0 or 1, and n+m=2. In preferred embodiments, the first reaction step produces a reaction product comprising at least 1,1,1,2,2-pentafluorpropane (HFC-245cb) and 2-chloro-1,1,1,2-tetrafluoropropane (HCFC-244).

In certain preferred embodiments, the fluorine addition step comprises contacting, (preferably by introducing into a reactor) the fluorination agent, preferably in excess amount, and even more preferably in an amount that is at least 1.5 times the amount required for reaction stoichiometry, and the compound of formula (I). In preferred embodiments the compound fluorine addition agent comprises HF and the formula I compound comprises $CF_3CCl=CH_2$.

In general a continuous gas phase reaction is preferred for the fluorine addition step. It is contemplated, however, that in certain embodiments it may be desirable to have this reaction step can be carried out in the liquid phase or in a combination of gas and liquid phases, and it is contemplated that the reaction can also be carried out batch wise, semi-continuous, or a combination of these.

Thus, it is contemplated that the halogen addition step may be performed using a wide variety of process parameters and process conditions in view of the overall teachings contained herein. However, it is preferred in certain embodiments that this single step reaction comprise a gas phase reaction, preferably in the presence of catalyst, preferably a metal catalyst, and most preferably an antimony-based catalyst. In highly preferred embodiments, the catalysts comprises, and preferably in proportion of at least about 30% by weight on the basis of the total catalyst in the reactor, at least one antimonyhalide, more preferably one or more antimonychlorides, and even more preferably antimonypentachloride ($SbCl_5$). In certain preferred embodiments, the catalysts comprises 50 wt % $SbCl_5$ on carbon. Other catalysts may also be used. For example, it is contemplated that the catalyst may comprise one or more transition metal-based catalysts (including, for example, transition metal halide catalysts, such as $FeCl_3$ and $TiCl_4$) and tin-based catalysts, such as $Sn_4Cl$. All the catalysts may be used in bulk and/or they may be supported, for example on carbon. It is contemplated that many other catalysts may be used depending on the requirements of particular embodiments. Of course, two or more of any of these catalysts, or other catalysts not named here, may be used in combination.

Applicants have found that pretreatment of the catalyst, particularly and preferably the antimonychloride-based catalyst, is highly preferred in certain preferred embodiments. The pretreatment step in the preferred embodiments comprises exposing the catalyst to at least one halogen-containing molecule, preferably at least one molecule containing F and/or Cl. In preferred embodiments, the catalyst is pretreated by flowing a pre-treating gas over the active surface of the catalyst, preferably at a temperature of greater than about 50° C. and preferably for a period of at least two hours and even more preferably for a period of at least four hours.

In certain preferred embodiments, the pre-treatment gas comprises HF and/or $Cl_2$. The pretreatment can take many forms, but in preferred embodiments the pretreatment comprises treating the catalyst first with a gas comprising, and preferably consisting essentially of HF, and then treating the catalyst with a second gas comprising, and preferably consisting essentially of, HF and $Cl_2$. It is also generally preferred that after pretreatment, the catalyst is swept with an inert gas, such as nitrogen, to substantially remove free halogen, and in particular free chlorine, from the catalyst.

While it is contemplated that a wide variety of reaction temperatures may be used, depending on relevant factors such as the catalyst being used and the most desired reaction product, it is generally preferred that the reaction temperature for the fluorine addition step is from about 20° C. to about 600° C., preferably about 50° C. to about 550° C., and even more preferably from about 300° C. to about 550° C.

In general, it is also contemplated that a wide variety of reaction pressures may be used, depending again on relevant factors such as the specific catalyst being used and the most desired reaction product. The reaction pressure can be, for example, superatmospheric, atmospheric or under vacuum, with a reactor pressure of from about 0 to about 10 psig being preferred in certain embodiments.

B. Separation of Fluorinating Agent

Although it is contemplated that in certain embodiments the reaction product from the first reaction step may be introduced, without substantial further processing, into the second reaction step of the present invention, it is generally preferred to use an intermediate processing step directed toward the removal of un-reacted starting materials, and/or other undesirable by-products, from the reaction stream prior to introducing the reaction products into the second reaction stage. For example, it is contemplated that un-reacted fluorine addition agent, such as HF, is preferably removed from the reaction product from the first reaction step prior to introducing the desired compound(s) of formula (B) to the second reaction stage. This removal step may include, for example, introducing the reaction product into a separation or extraction unit, preferably a packed column containing a scrubbing agent, such as NaF, KF, and/or $Al_2O$, to separate the fluorinating agent (preferably HF) from the reaction product stream. Preferably in such embodiments, the scrubbing column is maintained at a temperature of from about 50° C. to about 75° C. in order to obtain a high absorption efficiency. Alternatively, a scrubber solution, such as aqueous KOH, preferably in a concentration of from about 20 weight percent to about 60 weight percent, can be used to scrub the fluorinating agent (preferably HF) from the reaction product stream from the first stage of reaction.

C. Dehydrohalogenation

The methods of the present invention preferably comprise contacting a compound of formula (B) produced in the first reaction stage with a dehydrohalogenation agent to produce a fluoroolefin, preferably a C3 or C4 fluoroolefin, more preferably a compound of formula (II), and even more preferably tetrafluoropropene.

In certain preferred embodiments, the present dehydrohalogenation step is carried out under conditions effective to provide an average conversion of formula (II) compounds of at least about 40%, more preferably at least about 55%, and even more preferably at least about 70%. In certain preferred embodiments the conversion is at least about 90%, and more preferably about 100%. Further in certain preferred embodiments, the conversion of the compound of formula (B) to produce a compound of formula II is conducted under conditions effective to provide a formula II selectivity of at least about 25%, more preferably at least about 40%, more preferably at least about 70%, and even more preferably at least about 90%.

This reaction step can be carried out in the liquid phase or in the gas phase, or in a combination of gas and liquid phases, and it is contemplated that the reaction can be carried out batch wise, continuous, or a combination of these. However, in certain highly preferred embodiments, the second stage of reaction is carried out substantially in the gas phase.

Thus, it is contemplated that the dehydrohalogenation reaction step may be performed using a wide variety of process parameters and process conditions in view of the overall teachings contained herein. However, it is preferred in certain embodiments that this reaction step comprise a gas phase reaction, preferably in the presence of catalyst, preferably carbon, and even more preferably activated carbon. Other catalysts may be used, either alone or in conjunction one another or the preferred activated carbon catalyst. For example, it is contemplated that, antimony-based catalysts (such as $Sb/Cl_5$) and/or aluminum-based catalyst (such as $AlF_3$ and $Al_2O_3$), may also be used to advantage in certain embodiments of the present invention in the second reaction stage. It is expected that many other catalysts may be used depending on the requirements of particular embodiments, including for example palladium-based catalyst, platinum-based catalysts, rhodium-based catalysts and ruthenium-based catalysts.

The preferred gas phase dehydrohalogenation reaction may be conducted, for example, by introducing a gaseous form of a compound of formula (b) into a suitable reaction vessel or reactor. Preferably the vessel is comprised of materials which are resistant to corrosion, such as Hastelloy, Inconel, Monel and/or fluoropolymers linings. Preferably the vessel contains catalyst, for example a fixed or fluid catalyst bed, packed with a suitable dehydrohalogenation catalyst, with suitable means to heat the reaction mixture to the desired reaction temperature.

While it is contemplated that a wide variety of reaction temperatures may be used, depending on relevant factors such as the catalyst being used and the most desired reaction product, it is generally preferred that the reaction temperature for the dehydrohalogentation step is from about 100° C. to about 300° C., preferably about 120° C. to about 200° C., and even more preferably from about 140° C. to about 190° C.

In general it is also contemplated that a wide variety of reaction pressures may be used, depending again on relevant factors such as the specific catalyst being used and the most desired reaction product. The reaction pressure can be, for example, superatmospheric, atmospheric or under vacuum. Pressures of from about zero to about 100 psig are preferred in certain embodiments.

It is contemplated that in certain embodiments, an inert diluent gas, such as nitrogen, may be used in combination with the compound of formula (B). When such a diluent is used, it is generally preferred that the compound of formula (B) comprise from about 5 to greater than 95% by weight based on the combined weight of diluent and formula (B) compound(s).

It is contemplated that the amount of catalyst use will vary depending on the particular parameters present in each embodiment.

For embodiments in which the desired product of formula (II) is HFO-1234yf, it is preferred that the compound of formula (B) comprises at least one compound of formula (B1), namely,

where Y, n and m are as described above in connection with formula (B1), and particularly 1,1,1,2,2-pentafluorpropane (HFC-245cb) and/or 2-chloro-1,1,1,2-tetrafluoropropane (HCFC-244). Applicants have found that in such embodiments it is preferred to use as the catalyst an activated carbon. In addition, it is generally preferred in such embodiments to conduct at least a substantial portion of the reaction at a temperature of from about 100° C. to about 700° C. In certain preferred embodiments a reactor temperature of from about 100 to about 250° C., more preferably from about 140 to about 190° C. is used. In other embodiments, the reactor temperature is maintained at from about 400° C. to about 600° C.

Preferably the overall conversion, that is, the conversion considering both reaction stages, of the compound of formula (I) is at least about 50%, more preferably at least about 65%, and even more preferably at least about 90%. Preferably, the overall selectivity to compounds of formula (II), and in particular HFO-1234yf, is at least about 50%, more preferably at least about 70% and more preferably at least about 75%.

EXAMPLES

Additional features of the present invention are provided in the following examples, which should not be construed as limiting the claims in any way.

These examples illustrate gas phase fluorination in a first stage and a gas phase dehydrofluorination, using $CF_3CCl=CH_2$ to produce $CF_3CF=CH_2$ (1234yf).

A 22-inch (½-inch diameter) Monel tube reactor was charged with 120 cc of catalyst, as specified in Table I below. The reactor was mounted inside a heater and a temperature was observed using thermocouples kept at the middle, inside of the reactor. The inlet of the reactor was connected to a pre-heater, which was kept at about 300° sea by electrical heating. Organic feed material (specifically HFCO-1233xf) was introduced into the reactor from a cylinder maintained at about 70° C. The fluorine addition agent, namely, HF, was maintained in a cylinder at a substantially constant pressure of 45 psig introduced into the reactor after pre-heating. All reactions were run at a substantially constant pressure ranging from about zero to about 100 psig. In certain of the examples N2 was used as a diluent and fed to the reactor from a cylinder after preheating. The reactor temperature was brought to the temperature indicated in the table. The catalyst in the first reactor was pretreated at first with 50 g/h HF at about 65° C. for about four hours, and then with a combination of about 50 g/h HF and 200 sccm of Cl2 at about 65° C. for about four hours. After pre-treatment, 50 sccm of nitrogen gas was introduced into the catalyst for a period of about 40 minutes to sweep free chlorine from the catalyst surface prior to introducing the organic reactant. In many embodiments it was observed that reaction rates are undesirably low in the absence of catalyst pretreatment.

The product mixtures exiting from the first reaction stage as described above were passed through a packed column containing an HF removal agent (such as NaF, KF, or $Al_2O_3$) to separate unreacted HF from the reaction product stream the packed column was maintained at a temperature of from about 50° C. to about 75° C.

The reaction stream, after removal of HF, was then introduced into a second reactor containing 120 cc of activated carbon (preferably activated carbon provided by Calgon Corp.) maintained at a temperature of from about 400° C. to about 600° C. Preferably the reaction product exiting the second stage of reaction was treated to remove unwanted byproducts, for example HF or HCl. The effluent from the scrubber solution was then condensed to collect the products. The desired product $CF_3CF=CH_2$ (1234yf) was then isolated from the mixture by distillation.

The results are shown in Table I below.

TABLE 1

| Ex. # | Catalyst (Reactor 1) | Reactor 1 Temp., ° C. | Catalyst (Reactor 2) | Reactor 2 Temp. ° C. | % Conversion of 1233xf | % Selectivity to 1234yf |
|---|---|---|---|---|---|---|
| 1 | 50 wt % SbCl$_5$/C | 152 | Calgon Activated Carbon | 400 | 83 | 55 |
| 2 | 50 wt % SbCl$_5$/C | 155 | Calgon Activated Carbon | 450 | 86 | 57 |
| 3 | 50 wt % SbCl$_5$/C | 153 | Calgon Activated Carbon | 500 | 89 | 59 |
| 4 | 50 wt % SbCl$_5$/C | 148 | Calgon Activated Carbon | 500 | 88 | 60 |
| 5 | 50 wt % SbCl$_5$/C | 156 | Calgon Activated Carbon | 550 | 90 | 77 |
| 6 | 50 wt % SbCl$_5$/C | 175 | Calgon Activated Carbon | 550 | 93 | 77 |

An additional example is performed in which HF was not separated from the reaction product stream from the first reactor prior to being introduced into the second reactor. This example demonstrates a desirability of conducting the intermediate separation step insofar as selectivity for such embodiments is believed to be substantially less than for many of such embodiments in which the intermediate separation step is conducted. For example, in the additional example without the intermediate separation step, selectivity to HFO-1234yf was found to be approximately only 50%, with all of the reaction conditions being substantially the same as indicated above.

Having thus described a few particular embodiments of the invention, various alterations, modifications, and improvements will readily occur to those skilled in the art. Such alterations, modifications, and improvements, as are made obvious by this disclosure, are intended to be part of this description though not expressly stated herein, and are intended to be within the spirit and scope of the invention. Accordingly, the foregoing description is by way of example only, and not limiting. The invention is limited only as defined in the following claims and equivalents thereto.

What is claimed is:

1. A method for preparing a fluorinated organic compound comprising converting at least one compound of formula (I):

$$CF_3CX^1=CH_2 \qquad (I),$$

to at least one compound of formula (II):

$$CF_3CF=CH_2 \qquad (II),$$

where $X^1$ is Cl, Br or I, and wherein the converting step comprises (1) a fluorination addition reaction comprising exposing said at least one compound of formula I to conditions effective to produce at least one compound in accordance with formula (B):

$$CF_3CYYCH_3 \qquad (B),$$

where each Y is independently F, Cl, Br or I, provided that at least one Y is F, wherein said addition reaction is in the presence of at least one optionally supported fluorination catalyst selected from the group consisting of at least one antimony-based catalyst, at least one transition metal-based catalyst, at least one tin-based catalyst, and combinations thereof, and (2) a dehydrohalogenation reaction in the presence of at least one optionally supported dehydrohalogenation catalyst selected from the group consisting of activated carbon, at least one antimony-based catalyst, at least one aluminum-based catalyst, at least one palladium-based catalyst, at least one platinum-based catalyst, at least one rhodium-based catalyst, at least one ruthenium-based catalyst, and combinations thereof, wherein said reaction comprises exposing said compound of formula (B) to conditions effective to produce at least one compound in accordance with formula (II).

2. The method of claim 1 wherein said dehydrohalogenation reaction is a dehydrochlorination reaction.

3. The method of claim 1 wherein said compound of formula (I) comprises $CF_3CCl=CH_2$.

4. The method of claim 3 wherein said compound of formula (B) produces a reaction product comprising at least one compound of formula (B1):

$$CF_3CF_nY_mCH_3 \quad (B1),$$

where Y is F, Cl, Br or I, n is 1 or 2, m is 0 or 1, and n +m =2.

5. The method of claim 4 wherein said compound of formula (B1) comprises at least one of $CF_3CF_2CH_3$ and $CF_3CFClCH_3$.

6. The method of claim 5 wherein said at least one compound of formula (B1) comprises $CF_3CF_2CH_3$.

7. The method of claim 5 wherein said at least one compound of formula (B1) comprises $CF_3CFClCH_3$.

8. A method for preparing a fluorinated organic compound comprising converting at least one compound of formula (I):

$$CF_3CX^1=CH_2 \quad (I),$$

to at least one compound of formula (II):

$$CF_3CF=CH_2 \quad (II),$$

where $X^1$ is Cl, Br or I, and wherein the converting step comprises (1) a fluorination addition reaction comprising fluorinating said at least one compound of formula I under conditions effective to produce at least one compound in accordance with formula (B):

$$CF_3CYYCH_3 \quad (B),$$

where each Y is independently F, Cl, Br or I, provided that at least one Y is F, in the presence of at least one optionally supported fluorination catalyst selected from the group consisting of at least one antimony-based catalyst, at least one transition metal-based catalyst, at least one tin-based catalyst, and combinations thereof, and (2) a dehydrohalogenation reaction in the presence of at least one optionally supported dehydrohalogenation catalyst selected from the group consisting of activated carbon, at least one antimony-based catalyst, at least one aluminum-based catalyst, at least one palladium-based catalyst, at least one platinum-based catalyst, at least one rhodium-based catalyst, at least one ruthenium-based catalyst, and combinations thereof, wherein said reaction comprises exposing said compound of formula (B) to conditions effective to produce at least one compound in accordance with formula (II).

9. A method of preparing fluorinated organic compounds comprising contacting a three-carbon olefin with a chlorine addition agent to produce a compound according to formula A:

$$CF_3CHClCH_2X^1 \quad (A),$$

dehydrohalogenating said compound according to formula (A) to form a compound according to formula (I):

$$CF_3CX^1=CH_2 \quad (I); and$$

converting said compound of formula I to a compound according to formula (II):

$$CF_3CF=CH_2 \quad (II),$$

where $X^1$ is Cl, Br or I, and wherein the converting step comprises a fluorination addition reaction in the presence of at least one optionally supported fluorination catalyst selected from the group consisting of at least one antimony-based catalyst, at least one transition metal-based catalyst, at least one tin-based catalyst, and combinations thereof followed by a dehydrohalogenation in the presence of at least one optionally supported dehydrohalogenation catalyst selected from the group consisting of activated carbon, at least one antimony-based catalyst, at least one aluminum-based catalyst, at least one palladium-based catalyst, at least one platinum-based catalyst, at least one rhodium-based catalyst, at least one ruthenium-based catalyst, and combinations thereof.

10. The method of claim 9 wherein said three-carbon olefin is 3,3,3-trifluoropropene.

11. A method for preparing a fluorinated organic compound comprising converting at least one compound of formula (I):

$$CF_3CX^1=CH_2 \quad (I),$$

to at least one compound of formula (II):

$$CF_3CF=CH_2 \quad (II),$$

where $X^1$ is Cl, Br or I, and wherein the converting step comprises (1) a fluorination addition reaction comprising exposing said at least one compound of formula I to conditions effective to produce at least one compound in accordance with formula (B):

$$CF_3CYYCH_3 \quad (B),$$

where each Y is independently F, Cl, Br or I, provided that at least one Y is F, wherein said addition reaction is in the presence of at least one optionally supported fluorination catalyst selected from the group consisting of at least one antimony-based catalyst, at least one transition metal-based catalyst, at least one tin-based catalyst, and combinations thereof, and (2) a dehydrohalogenation reaction in a reactor comprising a Hastelloy, Inconel, and/or Monel lining, wherein said reaction comprises exposing said compound of formula (B) to conditions effective to produce at least one compound in accordance with formula (II).

* * * * *